United States Patent
Kurata et al.

(10) Patent No.: US 6,642,428 B1
(45) Date of Patent: Nov. 4, 2003

(54) WATER-DECOMPOSABLE ABSORBENT ARTICLE

(75) Inventors: Nobuhiro Kurata, Kagawa (JP); Mitsuhiro Wada, Kagawa (JP); Megumi Tokumoto, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 325 days.

(21) Appl. No.: 09/659,491

(22) Filed: Sep. 11, 2000

(30) Foreign Application Priority Data

Sep. 16, 1999 (JP) .................................. 11-261689

(51) Int. Cl.[7] .................................................. A61F 13/15
(52) U.S. Cl. ................................................... 604/364
(58) Field of Search .......................... 604/364, 385.01

(56) References Cited

U.S. PATENT DOCUMENTS

| | | | |
|---|---|---|---|
| 3,406,688 A | 10/1968 | Cubitt | 128/284 |
| 3,510,587 A | 5/1970 | Marder | 128/284 |
| 3,636,952 A | 1/1972 | George | 128/287 |
| 3,804,092 A * | 4/1974 | Tunc | |
| 3,939,836 A * | 2/1976 | Tunc | |
| 4,333,464 A | 6/1982 | Nakano | 128/290 |
| 4,798,603 A * | 1/1989 | Meyer et al. | |
| 5,384,189 A * | 1/1995 | Kuroda et al. | |
| 5,509,913 A | 4/1996 | Yeo | |
| 5,722,966 A * | 3/1998 | Christon et al. | |
| 6,127,593 A * | 10/2000 | Bjorkquist et al. | |

FOREIGN PATENT DOCUMENTS

| | | |
|---|---|---|
| FR | 463186 | 2/1946 |
| JP | 05-025764 | 2/1993 |
| JP | 06-101154 | 4/1994 |
| JP | 08-019571 | 1/1996 |
| JP | 08-038547 | 2/1996 |
| JP | 09-228214 | 9/1997 |
| JP | 10-085258 | 4/1998 |

\* cited by examiner

*Primary Examiner*—Dennis Ruhl
(74) *Attorney, Agent, or Firm*—Darby & Darby

(57) ABSTRACT

Provided is a water-decomposable absorbent article including a water-decomposable back sheet, a water-decomposable absorbent layer, and a surface member covering the absorbent layer. The surface member has a plurality of water-retentive water-decomposable sheets laminated and bonded to each other by integration means for permitting to dissociate the water-decomposable sheets from each other when wetted.

15 Claims, 2 Drawing Sheets

WATER-DECOMPOSABLE ABSORBENT ARTICLE

BACKGROUND OF THE INVENTION

1. Field of the Invention

The present invention relates to a water-decomposable absorbent article for sanitary napkins, panty liners, disposable diapers, pads for urinary incontinence and the like.

2. Description of the Related Art

Conventionally, the absorbent articles such as the sanitary napkins, the panty liners, the disposable diapers, and the pads for urinary incontinence are widely used for serving as absorbing body wastes. The absorbent articles are discarded as wastes, after having been used. However, the wastes of such absorbent articles are increasing in these days, and their volume is now an object of public concern. In addition, it is troublesome to treat the used absorbent articles as the wastes. Accordingly, absorbent articles composed of water-decomposable components and capable of being disposed of in toilets after use are now under study.

Japanese Unexamined Patent Publication (Kokai) No. Heisei 9-228241 discloses a water-decomposable non-woven fabric usable for a top sheet of absorbent articles. This non-woven fabric can be obtained through water-jetting treatment of a fibrous web that comprises regenerated cellulose having a fiber length of from 4 to 20 mm and pulp. Japanese Unexamined Patent Publication (Kokai) No. Heisei No. 5-25764 discloses a water-decomposable non-woven fabric usable for a surface member of absorbent articles. This non-woven fabric can be obtained by bonding fibers together with an unsaturated carboxylate copolymer serving as a binder. Japanese Unexamined Patent Publication (Kokai) No. Heisei 8-38547 discloses a water-decomposable absorbent sanitary article. This sanitary article comprises a surface layer formed by adding polyvinyl alcohol as a binder to water-dispersible fibers, a water-dispersible absorbent layer, and a water-soluble film. Japanese Unexamined Patent Publication (Kokai) No. Heisei 6-101154 discloses a water-degradable non-woven fabric containing a cellulose derivative as a binder therein. It also discloses an absorbent article comprising a top sheet of the water-degradable non-woven fabric, an absorbent layer of a pulp fiber sheet, and a back sheet of a polyvinyl alcohol film. Japanese Unexamined Patent Publication (Kokai) No. Heisei No. 8-19571 discloses a water-decomposable absorbent sanitary article. This absorbent sanitary article comprises a top layer of a water-dispersible non-woven fabric, an absorbent layer comprising water-dispersible absorbent paper, and a back layer formed by laminating polymethyl methacrylate on a film made of polyvinyl alcohol. Japanese Unexamined Patent Publication (Kokai) No. Heisei 10-85258 discloses a water-decomposable top sheet for absorbent articles, which is formed of a non-woven fabric comprising pulp and synthetic fibers. The top sheet can be readily peeled off from the other part (the side parts formed of synthetic fibers) of the absorbent article to which it is bonded, and can be disposed of in flush toilets.

Water-decomposable absorbent articles and water-decomposable top sheets must have good decomposability in water and high strength, while the two properties are contradictory to each other. With the prior art products set forth above, the decomposability in water and the strength are both limited. Specifically, enhancing the decomposability in water of the sheets will inevitably lead to the reduction of the strength thereof. Accordingly, the requirements for attaining well-balanced, good decomposability in water and high strength of absorbent articles are severe, and it is difficult to continuously produce the absorbent articles having well-balanced decomposability in water and strength.

SUMMARY OF THE INVENTION

An object of the present invention is to provide an absorbent article of which a surface member has good decomposability in water and high strength.

According to one aspect of the invention, a water-decomposable absorbent article may comprise a water-decomposable back sheet, a water-decomposable absorbent layer, and a surface member covering the absorbent layer, wherein the surface member includes a plurality of water-retentive water-decomposable sheets laminated and bonded to each other by integration means for permitting to dissociate the water-decomposable sheets from each other when wetted.

In the absorbent articles of the invention, the water-decomposable surface member has realized two contradictory functions of high decomposability in water after use and high durability during use. Specifically, in the invention, at least two water-decomposable sheets, which, however, are not satisfactorily durable enough for practical use when used individually, are integrally laminated to form the surface member of the absorbent articles, so that the laminated surface member exhibits high strength while having good decomposability in water.

Preferably, the integration means comprises mechanical means for bonding the water-decomposable sheets to each other. In this case, the mechanical means is needling for processing the water-decomposable sheets to have through-holes under the condition where the water-decomposable sheets are laminated, so that fibers constituting each the water-decomposable sheet are entangled around the through-holes. On the other hand, the mechanical means may be embossing the water-decomposable sheets under the condition where the water-decomposable sheets are laminated.

Preferably, the integration means is bonding the water-decomposable sheets to each other with a water-soluble adhesive.

Also preferably, the integration means is bonding the water-decomposable sheets to each other through hydrogen bonding, while in dry.

It is preferable that, the ratio of the water retention of one water-decomposable sheet to that of another adjacent to the sheet falls between 40:60 and 60:40, when the surface member are wetted.

Preferably, the water-decomposable sheets constituting the surface member each contain from 30 to 100% by weight of hydrophilic fibers.

Also preferably, each water-decomposable sheet has a weight (Metsuke) falling between 10 and 60 g/m$^2$.

Also preferably, each water-decomposable sheet has a degree of decomposition in water of at most 100 seconds, measured according to JIS P-4501 using Magnetic Stirrer MM-ST manufactured by MITAMURA RIKEN CO., LTD. Also preferably, the surface member comprising a plurality of such water-decomposable sheets has a degree of decomposition in water of at most 100 seconds, measured according to JIS P-4501.

Also preferably, the surface member comprising at least two water-decomposable sheets bonded to each other by the integration has a tensile strength in dry of at least 1000 g/25 mm, measured according to JIS P-8113 using Tensile Tester AUTOGRAPH (AGK-IKNG) manufactured by SHIMADZU CORPORATION.

Also preferably, the surface member comprising at least two water-decomposable sheets has a tensile strength in wet of at least 200 g/25 mm measured according to JIS P-8135.

DESCRIPTION OF THE PREFERRED EMBODIMENTS

Figure 1:
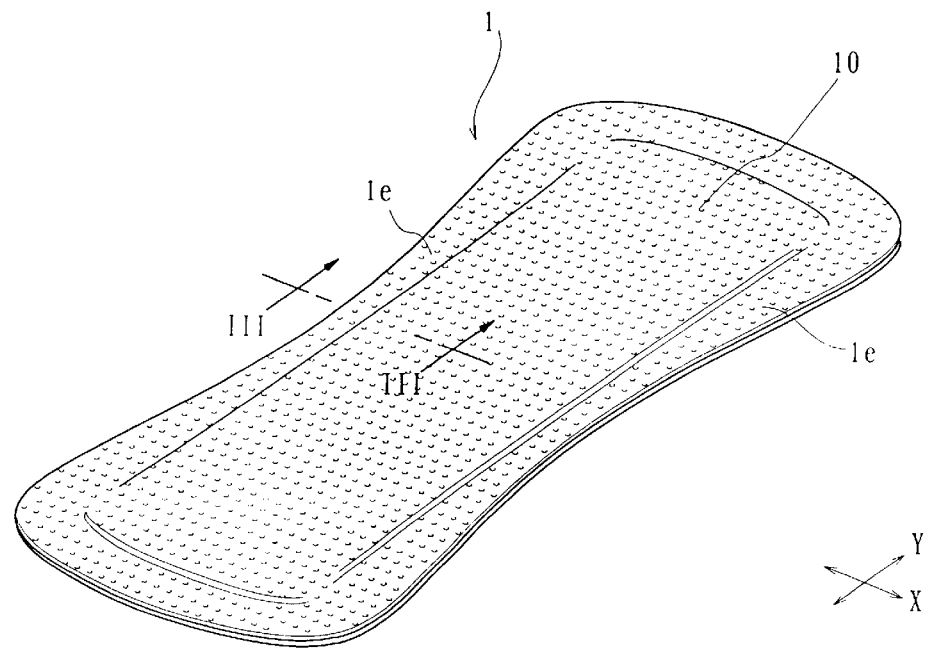
FIG. 1 is a perspective view showing one embodiment of an absorbent article of the invention.
Figure 2:
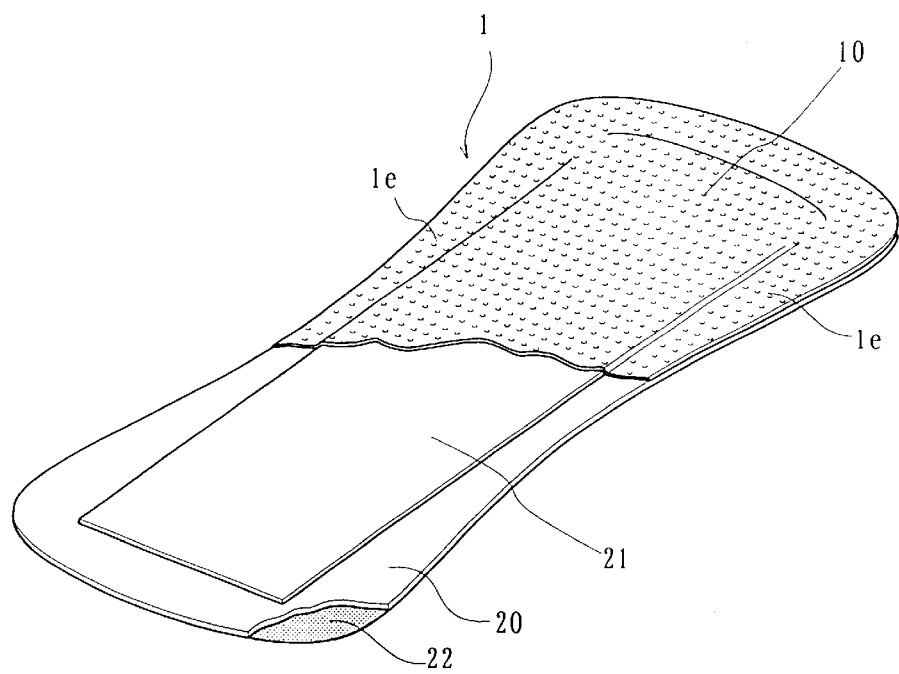
FIG. 2 is a partially cutaway perspective view showing partial cross section of the absorbent article of FIG. 1.
Figure 3:
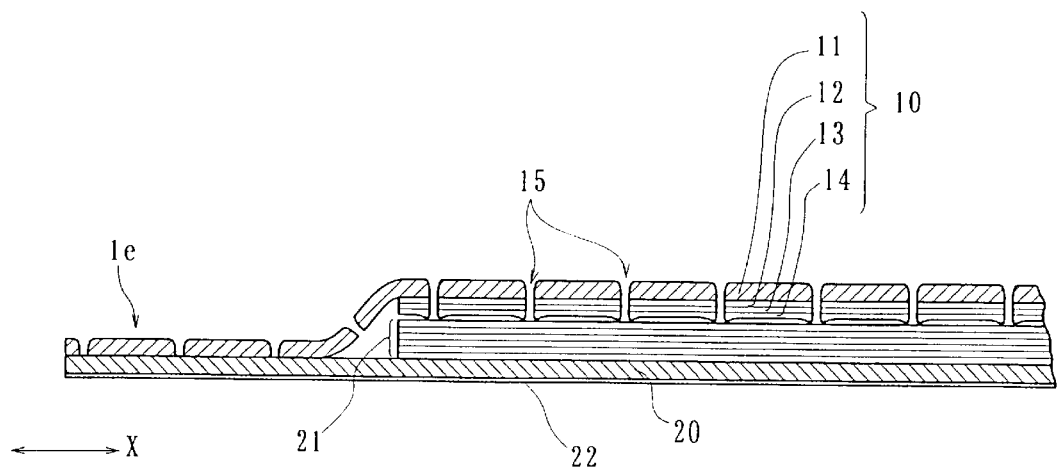
FIG. 3 is an enlarged cross-sectional view of FIG. 1 cut along the line III—III.
Figure 4:
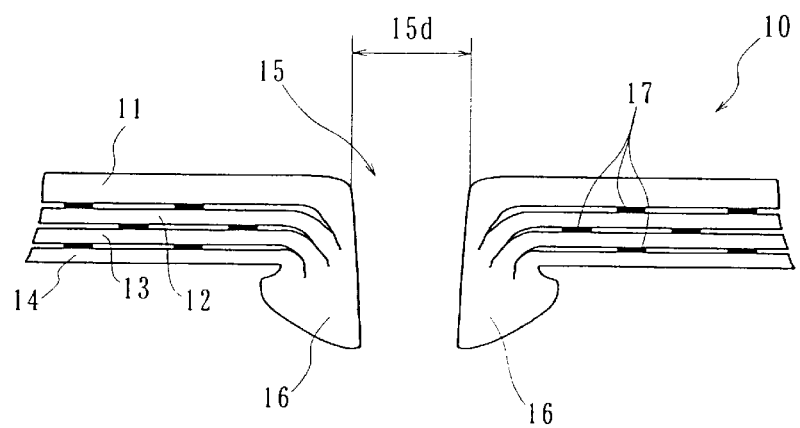
FIG. 4 is a partially enlarged cross-sectional view of a surface member of the absorbent article in FIG. 1.

The invention will be described hereinafter with reference to the accompanying drawings. FIG. 1 is a perspective view showing one embodiment of an absorbent article of the invention. FIG. 2 is a partially cutaway perspective view showing partial cross section of the absorbent article of FIG. 1. FIG. 3 is an enlarged cross-sectional view of FIG. 1 cut along the line III—III. FIG. 4 is a partially enlarged cross-sectional view of a surface member of the absorbent article in FIG. 1. It should be noted that X indicates the lengthwise direction of the absorbent article illustrated, and Y indicates the widthwise direction thereof that is substantially perpendicular to the direction X.

The absorbent article of FIG. 1 is a sanitary napkin or a panty liner, and this is one embodiment of a water-decomposable absorbent article of the invention that comprises a water-decomposable surface member of the invention. As shown in FIG. 2, the absorbent article 1 of FIG. 1 comprises a water-decomposable surface member 10 which is to be directly attached to a wearer, a water-decomposable back sheet 20, and a water-decomposable absorbent layer 21 sandwiched between the surface member 10 and the back sheet 20. More specifically, the surface member 10 and the back sheet 20 are bonded to each other with a water-soluble adhesive or the like around the absorbent layer 21 to form a peripheral bonded area 1e therearound.

An adhesive is applied to the back side of a main body of the absorbent article 1. Upon wearing it, the absorbent article 1 is set on a crotch portion inside an underwear, and is bonded to the crotch portion by means of the adhesive on the back side of the main body. Preferably, a release film 22 is provided to protect the adhesive layer before use. Also preferably, the release film 22 is formed of a water-decomposable sheet.

The surface member 10 is formed by laminating at least two water-decomposable sheets. As shown in FIG. 4, the surface member 10 in the shown embodiment is formed of a laminate of four water-decomposable sheets 11, 12, 13 and 14.

The water-decomposable sheets 11, 12, 13 and 14 are, after disposed of in flush toilets, readily dispersed in flushing water flow or in water in septic tanks. For example, they may be any of water-decomposable sheet-like papers formed from pulp as a raw material, in which the pulp fibers are bonded to each other through hydrogen bonding; water-decomposable sheet-like papers formed from water-dispersible fibers such as pulp and rayon as raw materials, in which the fibers are bonded to each other with a water-soluble binder added thereto; water-decomposable sheet-like papers formed by entangling fibers; and water-decomposable non-woven fabrics formed of relatively short fibers, in which the fibers are entangled through water-jetting treatment.

The water-dispersible fibers for the sheet may be any of natural fibers of pulp such as wood pulp, Manila hemp, linter pulp, bamboo pulp, kenaf, etc.; regenerated fibers of rayon, etc.; synthetic fibers of polypropylene, polyethylene, etc. Among those, preferred are ground pulp, as being anywhere decomposable in water to some degree even though formed into thick sheets. If desired, the different types of the fibers such as pulp and rayon may be combined, for example.

The water-soluble binder that may be in the water-decomposable sheets for bonding the constituent fibers to each other includes, for example, polyvinyl alcohol, modified polyvinyl alcohols, alkyl celluloses such as carboxymethyl cellulose, methyl cellulose, etc., and also cationic aldehyde-modified polyacrylamide copolymers, etc. In case where a polyvinyl alcohol-type water-soluble binder or a cellulose-type water-soluble binder is used in the water-decomposable sheets, an electrolyte and a metal salt may be optionally added thereto in order to enhance the strength of the water-decomposable sheets. Furthermore, in case where an alkyl cellulose-type water-soluble binder is used therein, an acrylic acid resin copolymer and an amino acid derivative may be added thereto for enhancing the strength of the water-decomposable sheets.

For preparing the water-decomposable non-woven fabrics of relatively short fibers in which the fibers are entangled through water-jetting treatment, for example, a mixture of rayon fibers having a length of from 2 to 20 mm, preferably from 3 to 10 mm and pulp, or the mixture additionally containing fibrillated rayon is formed into a fibrous web, and the resulting fibrous web is subjected to water-jetting treatment so that the constituent fibers are mutually entangled to a desired degree.

Preferably, the basis weight of each water-decomposable sheet falls between 10 and 60 g/m$^2$. If its basis weight is larger than 60 g/m$^2$, the water-decomposable sheet will be hard. Absorbent articles comprising such hard water-decomposable sheets will have a rough feel. On the other hand, if its basis weight is at most 10 g/m$^2$, the water-decomposable sheet will be too thin. Such thin water-decomposable sheets suffer from a lack of workability, and are often difficult to handle. In addition, they are not durable during use.

A plurality of the water-decomposable sheets set forth above are laminated to form the surface member of the invention. The plurality of the water-decomposable sheets 11, 12, 13 and 14 shown in FIG. 4 may be made from the same material, or may be made from different materials. Furthermore, the weight thereof may be all the same, or the sheet having a different weight may be combined. Preferably, however, the water-decomposable sheets 11, 12, 13 and 14 are controlled so that the decomposability of each sheet in water, measured according to JIS P-4501, is at most 100 seconds to permit the water-decomposable sheets to be disposed of in flush toilets and the like, similarly to toilet papers.

With the surface member 10 shown in FIG. 3, the uppermost water-decomposable sheet 11, which directly receives fluid, is a water-decomposable non-woven fabric of wet-spun lace having a basis weight of 45 g/m$^2$. The remaining three water-decomposable sheets 12, 13 and 14 are all of water-decomposable paper, each having a basis weight of 14 g/m$^2$.

The surface member 10 of the absorbent article 1 of the invention is formed by laminating the plurality of the water-decomposable sheets 11, 12, 13 and 14, and integrating them by means of wet-dissociative integration ("wet-dissociative integration" means that the integrated constituent sheets are readily dissociated from each other when the surface member is wetted with a large amount of water). As composed of the plurality of the water-decomposable sheets all integrated and bonded together by the means of wet-dissociative integration, the sheet strength of the surface member 10 is high. These water-decomposable sheets thus bonded together through wet-dissociative integration are, when wetted with water, separated from each other into individual ones, so that the decomposability in water of the surface member 10 is not degraded.

The means of wet-dissociative integration may include mechanical means for needling the plurality of the water-decomposable sheets, or mechanical means for embossing to spotwise press the plurality of the water-decomposable sheets optionally under heat.

In case where a plurality of water-decomposable sheets are needled, they shall have a lot of through-holes, and the constituent fibers are mutually entangled around the through-holes whereby the sheets are bonded to each other. Furthermore, in case where the plurality of the water-decomposable sheets are embossed, they are spotwise bonded to each other at the embossed spots as the constituent fibers are entangled in and around the embossed spots. As the case may be, the fibers constituting the water-decomposable sheets may be bonded to each other through hydrogen bonding in and around the embossed spots. The mechanical means employable herein for wet-dissociative integration of the plurality of the water-decomposable sheets to form the surface member includes all of the means adapted for mechanically entangling the fibers constituting the water-decomposable sheets.

As another means of wet-dissociative integration of the plurality of the water-decomposable sheets to form the surface member, the sheets may be also partially bonded to each other with a water-soluble adhesive. As further means thereof, the water-decomposable sheets may be bonded to each other through hydrogen bonding.

The mechanical means, the means for bonding with the water-soluble adhesive and the means for forming hydrogen bonding, as the means of wet-dissociative integration of water-decomposable sheets, may be employed either singly or as combined.

In the surface member 10 shown in FIG. 3 and FIG. 4, the water-decomposable sheets 11, 12, 13 and 14 are bonded to each other by the means of wet-dissociative integration, for which are combined the mechanical means for needling and the means for bonding with the water-soluble adhesive.

Concretely, the water-decomposable sheets 11, 12, 13 and 14 are, under the condition where the water-decomposable sheets are laminated in that order, needled in such a manner that the needles could penetrate through them from the top side serving as directly receiving fluid in actual use, thereby having through-holes 15 entirely throughout the surface member of the laminate of the sheets. As shown in the enlarged cross-sectional view of FIG. 4, the constituent fibers of the water-decomposable sheet having existed in the position of the through-holes 15 are pushed aside to be cut. In that condition, the constituent fibers around the through-holes 15 are entangled so that an entangled portion 16 around the respective through-holes protrudes to the backside of the surface member 10. Accordingly, the fibers can be physically or mechanically entangled around the through-holes 15. With the fibers thus entangled, the plurality of the water-decomposable sheets 11, 12, 13 and 14 are integrated all together to behave in integrated fashion, and form the surface member 10 having increased strength. Furthermore, the through-holes 15 have an additional function of leading fluid to the absorbent layer 21.

Preferably, a diameter $15d$ of the through-hole 15 is at most 3 mm. If the diameter $15d$ of the through-hole 15 exceeds the above-mentioned upper limit, the surface member will have a rough feel. In case where needles used in needling are tapered so that the diameter thereof becomes smaller at the tip, the diameter of the through-holes formed through the water-decomposable sheet 14 is to be smaller than that of the through-holes formed through the water-decomposable sheet 11. In this case, the preferable value of the diameter of the through-holes set forth above applies to the diameter of the through-holes formed through the water-decomposable sheet 11.

In order that the plurality of the water-decomposable sheets 11, 12, 13 and 14 to form the surface member 10 can behave in integrated fashion, it is desirable that a needle pitch, that is, the distance between the end of one through-hole 15 and that of another through-hole 15 adjacent thereto is at most 6 mm. If, however, the needle pitch for needling is smaller than 1 mm, the constituent fibers of the surface member 10 will be cut too short, and the strength of the surface member 10 may be lowered. On the other hand, if the needle pitch exceeds 10 mm, the number of the through-holes 15 to be formed will be decreased, so that the surface member 10 could not be well integrated to behave in integrated fashion. In case where any other means of wet-dissociative integration is employed except for needling, this needle pitch limitation shall not be applied thereto.

To further increase the strength of the surface member 10, it is desirable that the water-decomposable sheets 11, 12, 13 and 14 to form the surface member 10 are partly bonded to each other with a water-soluble adhesive 17. The method of applying the water-soluble adhesive 17 to the sheets and the area to be coated with the adhesive are not specifically defined. With the increase in the application amount of the adhesive, the surface member 10 will be harder. In view of the soft feel and the strength of the surface member 10, it is desirable that the water-soluble adhesive 17 is applied to the sheets in discontinuous spots or lines. When brought into contact with a large amount of water, the water-soluble adhesive 17 easily dissolves therein. Therefore, the water-soluble adhesive 17 can increase the strength of the surface member 10, without lowering the decomposability in water thereof.

It is not always necessary to apply the water-soluble adhesive 17 to all the water-decomposable sheets between them. For example, the water-decomposable sheets 12, 13 and 14 may be bonded to each other with the water-soluble adhesive, while the water-decomposable sheets 11 and 12 may not be bonded with the water-soluble adhesive.

The water-soluble adhesive 17 includes, for example, cellulose derivatives such as methyl cellulose, hydroxyethyl cellulose, carboxymethyl cellulose, etc.; water-soluble polymers such as polyvinyl alcohol, sodium alginate, sodium polyacrylate, polyacrylic acid esters, partially saponified products of polyacrylate copolymers, polyvinyl methyl ether, polyvinylpyrrolidone, copolymers of isobutylene and maleic anhydride, etc.; as well as starch, dextrin, etc.

As the plurality of the water-decomposable sheets 11, 12, 13 and 14 are integrated to form the surface member 10, they behave in integrated fashion as the integrated surface member 10 in actual use of the absorbent article 1. Accordingly, the strength of the surface member 10 is increased, and the resistance to breakage, distortion and abrasion thereof is increased accordingly.

When the surface member 10 is wetted with fluid of body wastes in actual use, the constituent sheets having been bonded to each other through mechanical needling or with the water-soluble adhesive 17 are released from each other, or the bonding force or the adhesiveness between them is degraded. In this case, if the water-decomposable sheets 11, 12, 13 and 14 constituting the surface member 10 are retentive of water, they can keep fluid therein and firmly adhere to each other via the water film formed between them. Accordingly, even when the bonding force for mechanically bonding to each other or the adhesive force between the constituent sheets with the water-soluble adhesive 17 is degraded in wetted condition, the sheets can maintain the integration of the constituent water-decomposable sheets 11, 12, 13 and 14 owing to the adhesiveness of the water film formed therebetween to prevent the strength of the surface member 10 from being significantly lowered.

To realize the adhesion of the constituent water-decomposable sheets by the water film formed between the sheets and to increase the wet strength of the surface member 10, it is desirable that the water retention of the adjacent sheets is substantially on the same level. The water retention referred to herein is meant to indicate the ratio of water absorbed and kept by the sheet (this is measured in a moisture regain measuring test) to the dry weight of the sheet. Preferably, the ratio of the water retention of one water-decomposable sheet to that of another adjacent to the sheet falls between 40:60 and 60:40, if the overall water retention of two adjacent sheets is defined as 100.

In case where the water retention of the two adjacent water-decomposable sheets is substantially on the same level as set forth above, the two sheets can be firmly adhered to each other owing to the water film spreading between surfaces of mutually opposing water-decomposable sheets. On the other hand, if there is a difference in the water retention between the two adjacent sheets, the fluid having been once absorbed by one sheet will be soon absorbed by the other sheet. Accordingly, it becomes difficult to form the water film between the two adjacent sheets.

The moisture regain measuring test is as follows: Two water-decomposable sheets of 100×100 mm in size are weighed individually, and laminated one on another. 1 cc of distilled water is dropped onto the center portion of the laminated sample. After left for 3 minutes, the two sheets are peeled without breaking them, and are again weighed individually. The water content of each wetted sheet is thus obtained. The ratio of the water content of the wetted sheet to the dry weight of the sheet indicates the water retention of the sheet set forth above.

In order that the water-decomposable sheets could have the ability to retain water to such a degree that the two adjacent sheets could be adhered to each other via the water film formed therebetween, it is desirable that the sheets respectively contain at least 30% by weight of pulp as hydrophilic fibers. In case where the pulp content thereof is smaller than 30% by weight, the water-decomposable sheet will be poorly retentive of water. The surface member 10 composed of such poorly water-retentive sheets could not enjoy the integrated behavior of the constituent sheets.

The back sheet 20 may be formed of water-decomposable non-woven fabric or paper. For example, it is a water-decomposable non-woven fabric of wet-spun lace composed of pulp and rayon, and having a basis weight of 45 g/m². The outer surface of the back sheet 20 may be coated with a water-soluble resin such as polyvinyl alcohol, an unsaturated carboxylic acid copolymer or the like. Thus coated, the back sheet 20 will be impervious to fluid.

The absorbent layer 21 is formed of, for example, water-decomposable paper, pulp or non-woven fabric. In cases where the absorbent layer 21 is formed of the water-decomposable paper, it is desirable that a plurality of relatively thin, water-decomposable papers are laminated to form it. The absorbent layer 21 thus formed of the water-decomposable paper in that manner well decomposes in water. For example, from 4 to 8, preferably 6 or so sheets of the water-decomposable paper each having a basis weight of 14 g/m² are laminated to form the absorbent layer 21. In cases where the back sheet 20 is not processed to be impervious to fluid, the lowermost layer of the water-decomposable paper constituting the absorbent layer 21 may be coated with the water-soluble resin and the like so as to be impervious to fluid. In cases where the surface member is thick, the absorbent layer may be omitted.

The water-decomposable surface member 10 is applicable not only to the sanitary napkins but also to the panty liners, the disposable diapers, the pads for the urinary incontinence or the like. Preferably, these absorbent articles are constituted so that all of the constituents thereof are decomposable in water to be disposed of in flush toilets or the like, after use.

EXAMPLES

The invention will be described in more detail with reference to the following Examples, which, however, are not intended to restrict the scope of the invention.

Using the following materials, water-decomposable surface members or water-decomposable sanitary napkins were prepared as shown in Table 1 and Table 2 below. The uppermost water-decomposable non-woven fabric of wet-spun lace used herein for the surface member had a basis weight of 45 g/m², and the remaining three water-decomposable papers 12, 13 and 14 had a basis weight of 14 g/m², respectively. For the absorbent layer, a water-decomposable paper having a weight of 30 g/m² was used. For the back sheet, a water-decomposable non-woven fabric of wet-spun lace having a basis weight of 45 g/m² was used. Some samples of the surface member were needled for integrating the constituent sheets. In these samples, the through-holes formed by needling all had a diameter of 1.5 mm, and the needle pitch was 1.5 mm. Some others were not needled, but were thermally embossed in wet throughout their surface for integrating the constituent sheets. Still others not needled were. processed with the water-soluble adhesive spirally applied to the constituent layers for integrating them. For these, the amount of the adhesive to be applied in spiral fashion between the adjacent layers was 5 g/m², and the diameter of one circle of the adhesive to be applied was about 18 mm. The surface members and the sanitary napkins thus prepared herein were tested for their properties according to the following test methods. The test data obtained are given in Table 1 and Table 2.

Tensile Strength:

The sample to be tested was cut into pieces each having a width of 25 mm and a length of 150 mm, and these were tested according to JIS P-8113 by the use of a Tensilon tester, for which the chuck distance was 100 mm and the stress rate was 100 mm/min. The strength at break (gf) of the sample thus measured indicates the tensile strength thereof (see the following Table—the data are expressed in g/25 mm).
Wet Tensile Strength:

The sample to be tested was wetted with water to have a water content of 2.5 times its dry weight, and cut into pieces each having a width of 25 mm and a length of 150 mm. These were tested according to JIS P-8135 using Tensile Tester AUTOGRAPH (AGK-IKNG) manufactured by SHIMADZU CORPORATION, for which the chuck distance was 100 mm and the stress rate was 100 mm/min. The strength at break (gf) of the sample thus measured indicates the wet tensile strength thereof (see the following Table—the data are expressed in g/25 mm).
Wear Test:

The sample to be tested was worn by 10 panelists for 3 hours. After having been thus worn, the condition of the surface member of the sample was macroscopically checked. The criteria for sample evaluation are as follows:

○: No change in the surface member.

Δ: The surface member was expanded.

X: The surface member was broken.
Decomposability in Water:

The test for decomposability in water of each sample was based on the water degradability test of JIS P-4501. Precisely, a test piece of the sample having a length of 10 cm and a width of 10 cm was put into a 300-ml beaker filled with 300 ml of ion-exchanged water, and stirred therein with a rotor. The revolution speed of the rotor was 600 rpm. The condition of the test piece being dispersed in water was macroscopically observed at predetermined time intervals, and the time until the test piece was dispersed was measured (the data are expressed in seconds).

As described in detail hereinabove, the water-decomposable surface member of the invention comprises a plurality of sheets that are highly decomposable in water, thereby having good decomposability in water and high strength.

The constituent sheets are integrated into the surface member by the means of wet-dissociative integration. Concretely, they are integrated by mechanically pressing them in such a manner that the fibers constituting them are mechanically entangled in the integrated laminate, or by adhering them to each other with the water-soluble adhesive, or by a combination of two means of integration. Therefore, in actual use, the sheets constituting the surface member behave in integrated fashion, so that the surface member is resistant to breakage, distortion and abrasion thereof. In actual use, the dry area of the surface member well keeps the integrated condition by the integration means set forth above. On the other hand, in the wetted area thereof, the constituent sheets well adhere to each other to keep effect of integration owing to the surface tension of the fluid therein, since the water retention of the respective constituent sheets is substantially the same level.

Furthermore, by using the surface member thus having good decomposability in water and high strength (both in wet and in dry), it becomes possible to constitute the water-decomposable absorbent articles having good decomposability in water and high strength.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features,

TABLE 1

|  | Example 1 | Example 2 | Comp. Example 1 | Comp. Example 2 |
| --- | --- | --- | --- | --- |
| Constitution of Surface Member | one sheet of wet-spun lace three sheets of water-decomposable papers | one sheet of wet-spun lace three sheets of water-decomposable papers | none three sheets of water-decomposable papers | one sheet of wet-spun lace none |
| Integration Means | needling | Adhesion with water-soluble adhesive | none | none |
| Tensile Strength | 1500 | 1550 | 800 | 1000 |
| Wet Tensile Strength | 210 | 200 | 49 | 175 |

TABLE 2

|  | Example 3 | Example 4 | Example 5 | Example 6 | Comp. Example 3 |
| --- | --- | --- | --- | --- | --- |
| Constitution of Surface Member | one sheet of wet-spun lace three sheets of water-decomposable papers | None six sheets of water-decomposable papers | one sheet of wet-spun lace three sheets of water-decomposable papers | one sheet of wet-spun lace three sheets of water-decomposable papers | none six sheets of water-decomposable papers |
| Constitution of Absorbent Layer | six sheets of water-decomposable papers | six sheets of water-decomposable papers | six sheets of water-decomposable papers | six sheets of water-decomposable papers | six sheets of water-decomposable papers |
| Constitution of Back Sheet | one sheet of wet-spun lace | one sheet of wet-spun lace | one sheet of wet-spun lace | one sheet of wet-spun lace | one sheet of wet-spun lace |
| Integration Means | needling | needling | embossing | adhesion with water-soluble adhesion | none |
| Wear Test | ○ | ○ | Δ | ○ | x |
| Decomposability in Water | 95 | 40 | 93 | 90 | 35 | integers, steps or components but does not preclude the presence or addition of one or more other features, integers, steps, components or groups thereof.

What is claimed is:

1. A water-decomposable absorbent article comprising:
   a water-decomposable back sheet;
   a water-decomposable absorbent layer; and
   a surface member covering the absorbent layer;
   the surface member comprising a plurality of water-retentive water-decomposable sheets laminated and bonded to each other by integration means for permitting the water-decomposable sheets to dissociate from each other when wet, and having a tensile strength of at least 1000 g/25 mm when dry.

2. A water-decomposable absorbent article comprising:
   a water-decomposable back sheet;
   a water-decomposable absorbent layer; and
   a surface member covering the absorbent layer;
   the surface member comprising a plurality of water-retentive water-decomposable sheets laminated and bonded to each other by integration means for permitting the water-decomposable sheets to dissociate from each other when wet, and having a tensile strength of at least 200 g/25 mm when wet.

3. The water-decomposable absorbent article as set forth in claim 1 or 2, wherein the integration means comprises mechanical means for bonding the water-decomposable sheets to each other.

4. The water-decomposable absorbent article as set forth in claim 3, wherein the mechanical means is needling for processing the water-decomposable sheets to provide through-holes, so that fibers constituting each water-decomposable sheet are entangled around the through-holes.

5. The water-decomposable absorbent article as set forth in claim 3, wherein the mechanical means is embossing the water-decomposable sheets.

6. The water-decomposable absorbent article as set forth in claim 3, wherein the mechanical means is bonding the water-decomposable sheets to each other with a water-soluble adhesive.

7. The water-decomposable absorbent article as set forth in claim 1 or 2, wherein the integration means is bonding the water-decomposable sheets to each other through hydrogen bonding.

8. The water-decomposable absorbent article as set forth in claim 1 or 2, wherein the ratio of the water retention of one water-decomposable sheet to that of another water-decomposable sheet adjacent to the sheet is in a range of between 40:60 and 60:40, when the surface member is wet.

9. The water-decomposable absorbent article as set forth in claim 8, wherein the water-decomposable sheets each contain from 30 to 100% by weight of hydrophilic fibers.

10. The water-decomposable absorbent article as set forth in claim 1 or 2, wherein the water-decomposable sheets each have a basis weight within a range of between 10 and 60 g/m$^2$.

11. The water-decomposable absorbent article as set forth in claim 1 or 2, wherein the water-decomposable sheets each have a degree of decomposition in water of at most 100 seconds.

12. The water-decomposable absorbent article as set forth in claim 11, wherein the surface member has a degree of decomposition in water of at most 100 seconds.

13. A water-decomposable absorbent article comprising:
    a water-decomposable back sheet;
    a water-decomposable absorbent layer; and
    a surface member covering the absorbent layer;
    said surface member comprising a plurality of water-retentive water-decomposable sheets laminated and bonded to each other by needling to provide through-holes, so that fibers constituting each water-decomposable sheet are entangled around said through-holes.

14. A water-decomposable absorbent article comprising:
    a water-decomposable back sheet;
    a water-decomposable absorbent layer; and
    a surface member covering the absorbent layer;
    said surface member comprising a plurality of water-retentive water-decomposable sheets laminated and bonded to each other by embossing said water-decomposable sheets.

15. A water-decomposable absorbent article comprising:
    a water-decomposable back sheet;
    a water-decomposable absorbent layer; and
    a surface member covering the absorbent layer;
    said surface member comprising a plurality of water-retentive water-decomposable sheets laminated and bonded to each other by bonding the water-decomposable sheets to each other through hydrogen bonding.

* * * * *